(12) United States Patent
Hall

(10) Patent No.: US 7,909,511 B2
(45) Date of Patent: Mar. 22, 2011

(54) TRAY FOR PORTABLE DIGITAL RADIOGRAPHY CASSETTE

(75) Inventor: John H. Hall, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 87 days.

(21) Appl. No.: 12/404,403

(22) Filed: Mar. 16, 2009

(65) Prior Publication Data

US 2010/0232575 A1 Sep. 16, 2010

(51) Int. Cl.
*H01J 31/50* (2006.01)
(52) U.S. Cl. .......................................... 378/189
(58) Field of Classification Search ............ 378/19, 378/98.8, 189; 250/370.11, 370.09
See application file for complete search history.

(56) References Cited

U.S. PATENT DOCUMENTS

| | | | |
|---|---|---|---|
| 5,661,309 A | 8/1997 | Jeromin et al. | 250/580 |
| 5,773,839 A | 6/1998 | Krepel et al. | 250/580 |
| 5,844,961 A | 12/1998 | McEvoy et al. | |
| 7,016,467 B2 * | 3/2006 | Brooks | 378/102 |
| 2004/0114725 A1 | 6/2004 | Yamamoto | |
| 2006/0034427 A1 | 2/2006 | Brooks | |
| 2006/0054833 A1 | 3/2006 | Tsuchino et al. | |
| 2006/0097177 A1* | 5/2006 | Yamamoto | 250/370.08 |
| 2008/0112535 A1 | 5/2008 | Wojcik et al. | |
| 2009/0028299 A1 | 1/2009 | Yoshimi et al. | |

FOREIGN PATENT DOCUMENTS

| | | |
|---|---|---|
| JP | 2004/180931 | 7/2004 |
| WO | WO 01/33921 | 11/1999 |

* cited by examiner

*Primary Examiner* — Irakli Kiknadze

(57) ABSTRACT

An apparatus for digital radiography has a cassette adapted to obtain a digital image of a subject in response to incident radiation when receiving source power through an input power connector and adapted to provide the obtained digital image as output from a first data connector. A support tray is adapted to removably seat the cassette and has a second data connector that releasably engages with the first data connector on the cassette when the cassette is seated in the support tray. A wireless communication circuit in the support tray is energizable to transmit the digital image obtained from first data connector of the cassette to a host processor. A battery in the tray provides source power to at least the wireless communication circuit on the support tray circuitry and the input power connector of the seated cassette.

20 Claims, 10 Drawing Sheets

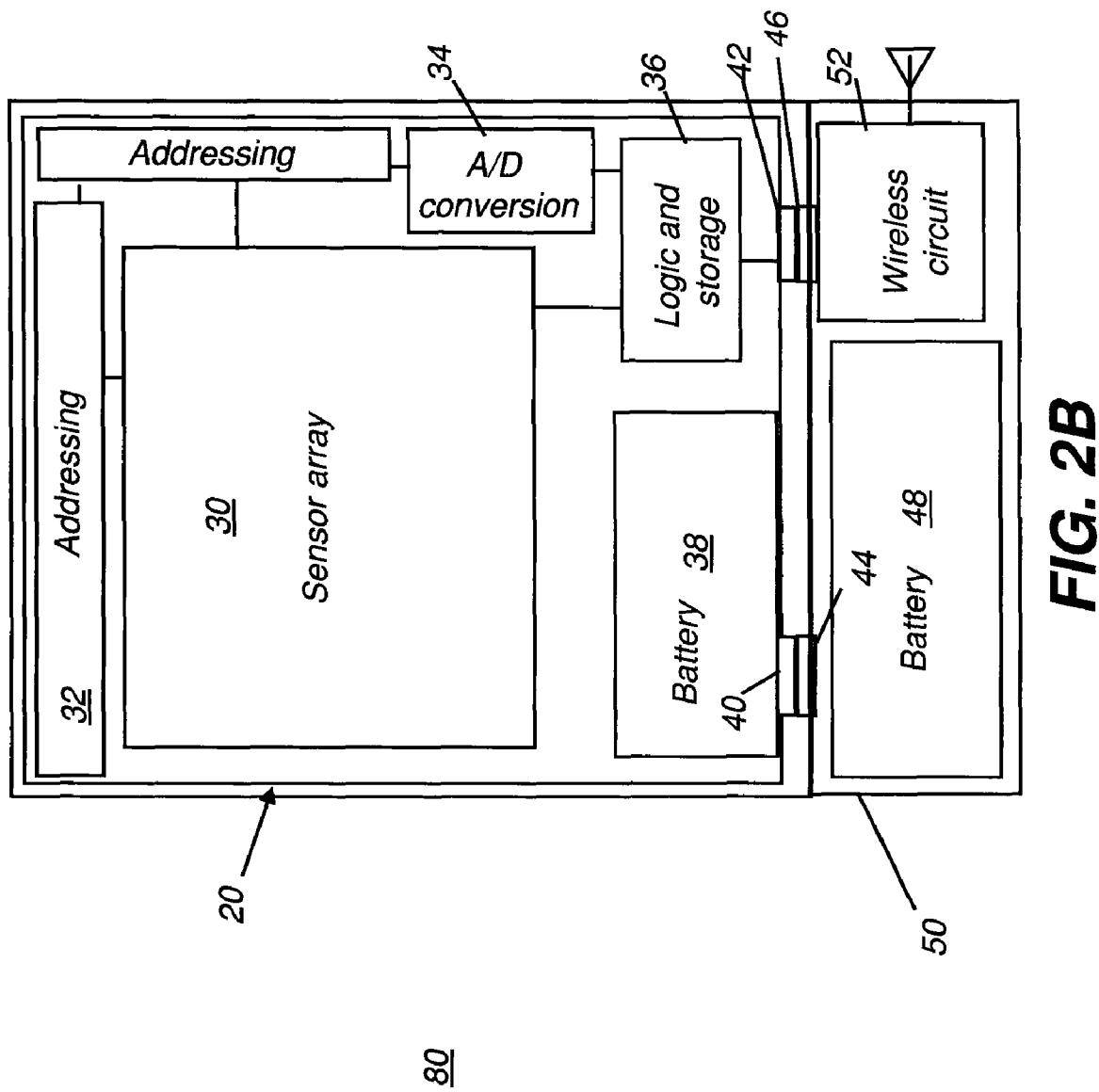

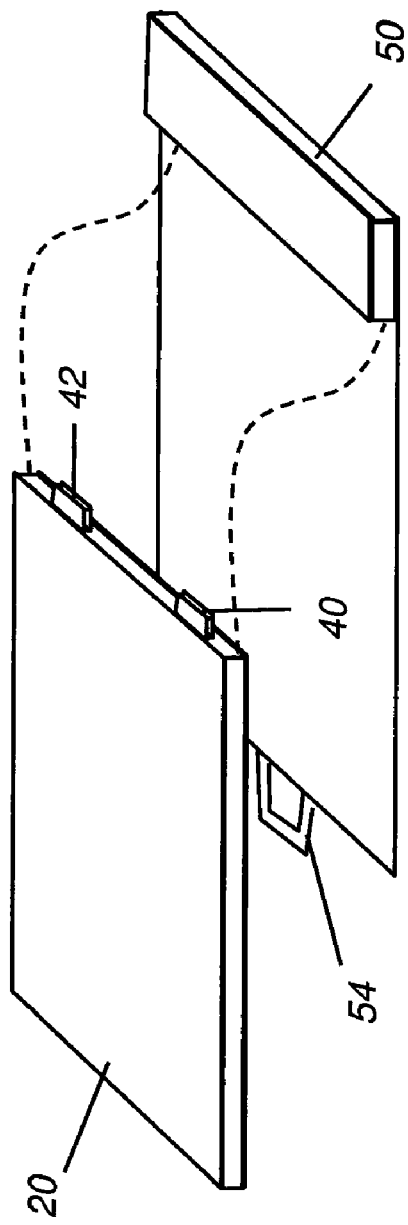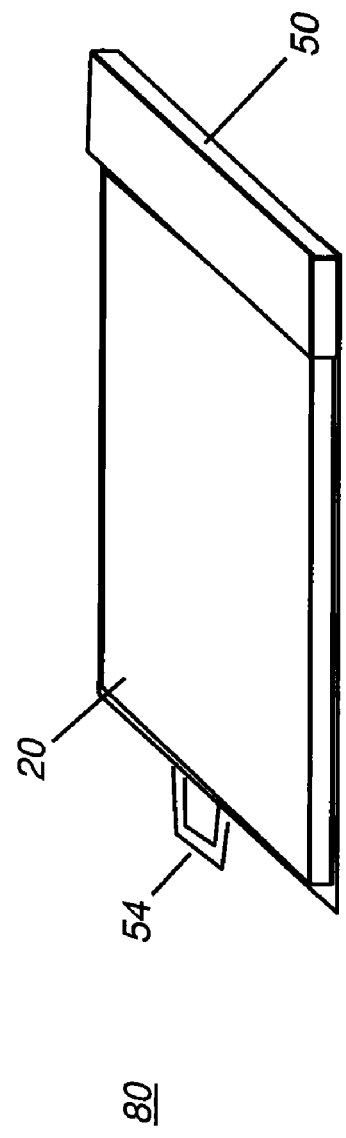
FIG. 3A
FIG. 3B

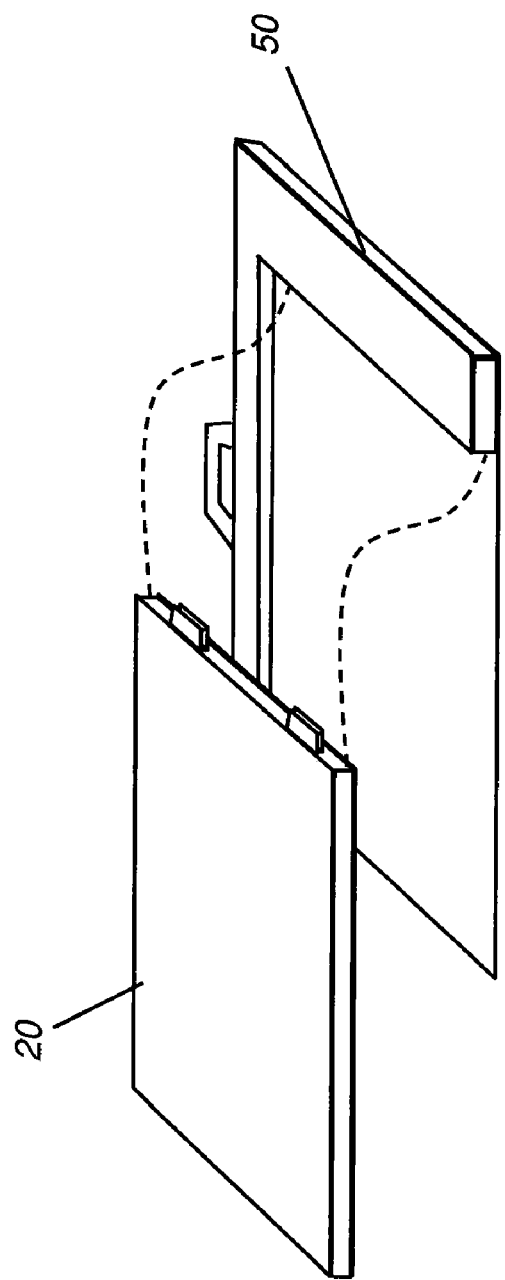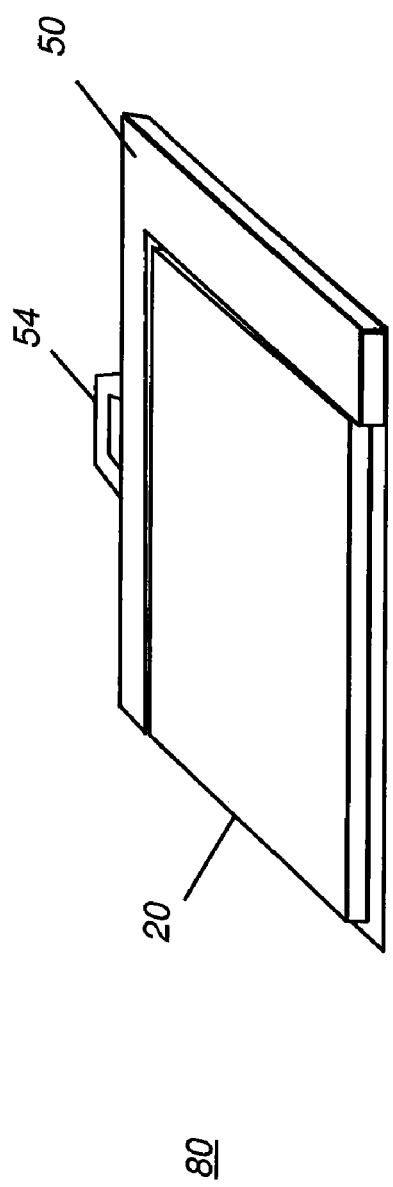

TRAY FOR PORTABLE DIGITAL RADIOGRAPHY CASSETTE

FIELD OF THE INVENTION

This invention generally relates to digital diagnostic imaging and more particularly relates to a support tray for a digital radiography cassette.

BACKGROUND OF THE INVENTION

Digital radiography (DR) is increasingly accepted as an alternative to either film-based or computed radiography (CR) imaging technologies that rely on photosensitive film layers or photostimulable storage phosphors to capture radiation exposure and thus to produce and store an image of a subject's internal physical features. With digital radiography, the radiation exposure energy captured on radiation-sensitive layers is converted, pixel by pixel, to electronic image data which is then stored in memory circuitry for subsequent readout and display on suitable electronic image display devices. Among the driving forces in the success of digital radiography is the ability to rapidly visualize and communicate stored images via data networks to one or more remote locations for analysis and diagnosis by the radiologist, without the delay that results when film is developed and checked, then packaged and mailed or sent by courier to a remote location or when the film is input to a separate scanner apparatus to provide digitized image data.

Flat panel digital radiographic (DR) imaging systems enjoy a number of advantages over conventional film-based or earlier computed radiography (CR) systems. Among its salient advantages is the capability of the DR system to obtain radiographic image data without the need for an operator or technologist to move, handle, process, or scan any type of imaging medium following exposure. Data downloaded directly from the DR receiver panel is then quickly available for viewing and diagnosis on-site or at any appropriately networked viewer workstation. Among its other advantages are the capability to work with existing hardware components that generate x-ray radiation and its reduced dependence on operator performance.

Due to their size, weight and expense, earlier flat panel digital radiographic (DR) imaging detectors were permanently mounted in table and wall bucky structures specially designed to accommodate them. Continuing improvements allow more compact and portable DR imaging cassettes that can be used with imaging systems that were originally designed for use with film and CR cassettes. It is envisioned that reduced weight and size may allow conformance of the DR cassette form factor to the ISO-4090 35×43 cm standard cassette profile. This would allow the DR cassette to be fitted into existing table or wall x-ray units that also conform to this standard and promises to expand the usability of DR detection as a retrofit to existing film and CR cassettes equipped x-ray rooms, obviating the need to upgrade or modify existing x-ray table and wall equipment, as is done currently, thus offering beneficial cost advantages. As a result, retrofit DR detectors would be usable with systems that are now limited only for use with film and CR detectors. Further, as the DR cassette is reduced in size and weight and thus becomes more portable, there are more potential applications for its use, including use of the DR cassette as a tethered device, that is, connected to a receiving system with one or more cables for power and data transmission, or even as an un-tethered device, capable of wirelessly transmitting image data to a nearby imaging apparatus, eliminating the need for a cumbersome interconnecting cable or cables.

In addition to reduced size and weight, it would be highly desirable to provide a truly portable digital detector that is untethered for wireless communication and contains on-board battery power. With these additional advantages, the portable DR detector can be easily retrofitted into existing x-ray imaging systems. This would help to provide a detector that can be readily moved from one location to another as needed, without the cumbersome requirements and risks imposed by the need to connect power or data cables.

While full portability of the DR cassette with wireless communication is a desirable goal, however, practical hurdles remain. Image capture components that sense received radiation and convert the sensed signal to digital data can be miniaturized and packaged within the DR cassette itself. However, it remains a challenge to compactly package the additional support circuitry that is needed in order to provide battery power for successive image captures and the circuitry that is needed for providing wireless communication with a remote system. Moreover, this full portability and untethered operation may not be necessary for all imaging systems; there can be systems for which tethered operation is fully acceptable.

Thus, it can be appreciated that there would be advantages to a DR cassette that can be used in either fully portable, untethered mode or with a tethered host and power supply connection.

SUMMARY OF THE INVENTION

It is an object of the present invention to advance the art of diagnostic imaging. With this object in mind, the present invention provides an apparatus for digital radiography comprising: a cassette adapted to obtain a digital image of a subject in response to incident radiation when receiving source power through an input power connector and adapted to provide the obtained digital image as output from a first data connector; and a support tray adapted to removably seat the cassette and comprising: (1) a second data connector that releasably engages with the first data connector on the cassette when the cassette is seated in the support tray; (2) a wireless communication circuit that is energizable to transmit the digital image obtained from first data connector of the cassette to a host processor; and (3) a battery providing source power to at least the wireless communication circuit on the support tray circuitry and the input power connector of the seated cassette.

It is a feature of the present invention that it provides a tray that holds supporting electronics and power circuitry for a portable DR cassette.

It is an advantage of the present invention it allows the use of the DR cassette in a number of alternative configurations, allowing tethered as well as untethered operation.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings.

FIG. 2B is a schematic diagram of a support tray for the portable DR cassette.

FIG. 3A is a perspective diagram showing how the DR cassette fits into the tray in one embodiment.

FIG. 3B is a perspective view showing the assembled DR cassette and tray for the embodiment of FIG. 3A.

FIG. 3C is a perspective diagram showing how the DR cassette fits into the tray in an alternate embodiment.

FIG. 3D is a perspective view showing the assembled DR cassette and tray for the embodiment of FIG. 3C.

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

Figures provided in this application are intended to show overall functional relationships and features and are not intended to be drawn to scale.

Figure 1B:
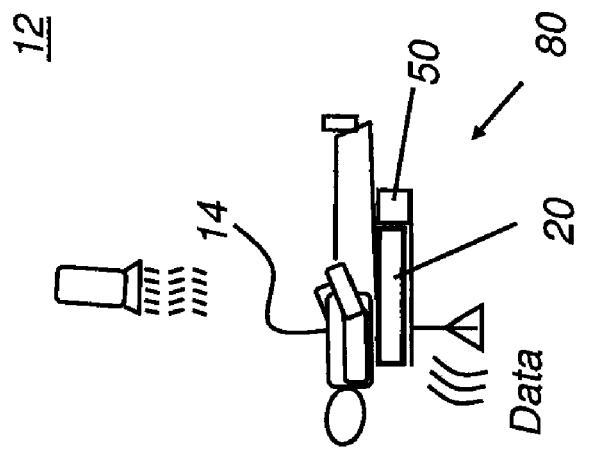
FIG. 1B is a schematic block diagram showing the use of a portable DR cassette in its support tray during exposure.
Figure 1B:
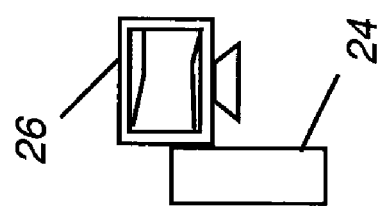
Figure 1A:
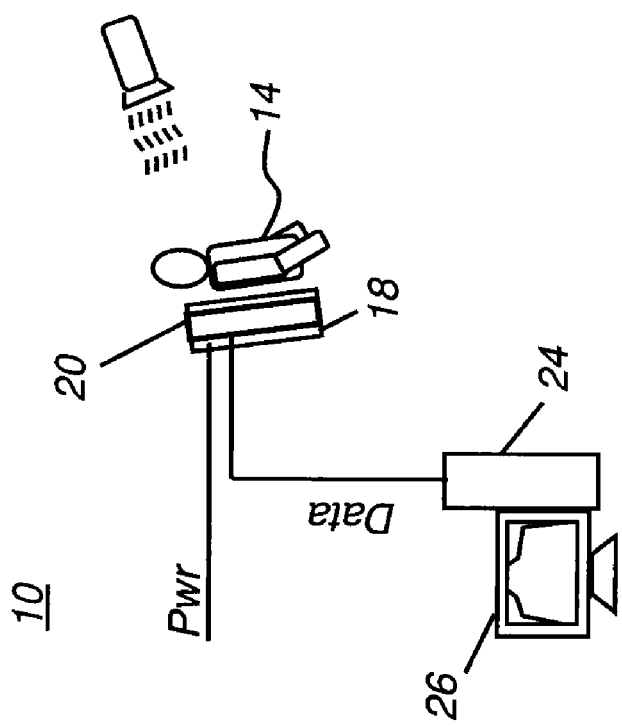
FIG. 1A is a schematic block diagram showing the use of a portable DR cassette in a tethered connection embodiment.
Figure 1C:
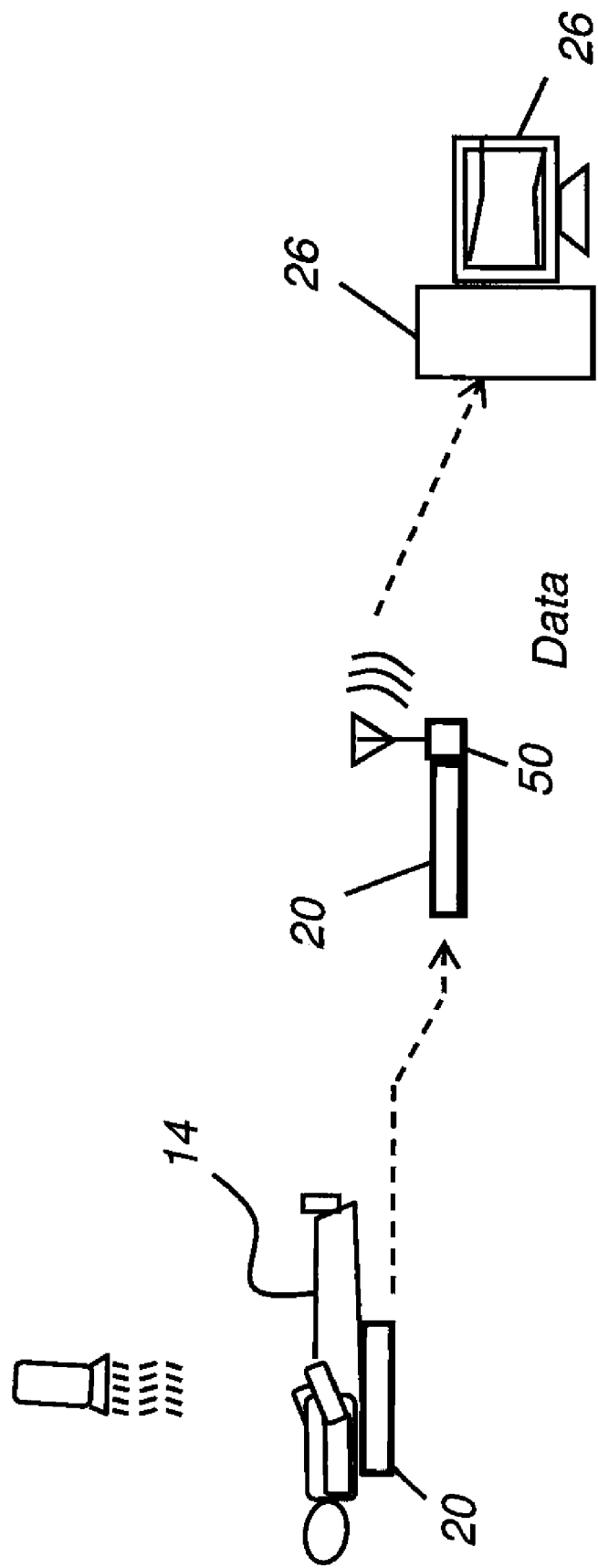
FIG. 1C is a schematic block diagram showing the use of the portable DR cassette removed from its tray during imaging and restored to the tray for wireless data transmission to the host.

Embodiments of the present invention provide a support tray for a DR cassette that expands the number of environments in which a portable DR cassette can be used. FIGS. 1A through 1C show a range of suitable environments that can be provided with DR imaging using the apparatus and methods of embodiments of the present invention.

FIG. 1A shows a radiographic imaging apparatus 10 for imaging a subject, such as a patient 14 in a tethered transmission mode. Radiographic imaging apparatus 10 has a bucky 18 and provides supporting power and data communication connections to a portable DR cassette 20 when it is installed in bucky 18. This type of environment can allow tethered, that is, cable-connected, operation, with power and data communication connections from cables to the bucky apparatus. The ISO-compatible form factor of the DR cassette 20 would be advantageous for such environments. Data is provided to an image data and storage processor, host processor 24 having a display 26.

FIG. 1B shows the use of DR cassette 20 in an alternate radiographic imaging apparatus 12 that does not provide tethered connection, but instead operates in a wireless transmission mode. For such an arrangement, DR cassette 20 can be used to obtain the radiation image data when mounted in a support tray 50. An imaging detector 80 that is formed from the combined DR cassette 20 and support tray 50 would not conform to the dimensions of a film-based or CR cassette. However, detector 80 would be usable for imaging under a number of different conditions, provided sufficient clearance space around detector 80 is available.

Support tray 50 provides an additional source of power for data acquisition and provides wireless data communication to host processor 24. In embodiments of the present invention, the same DR cassette 20 can be used in either or both the tethered DR cassette 20 configuration shown in FIG. 1A and the detector 80 configuration shown in FIG. 1B. Support for the "standalone" configuration shown in FIG. 1C is optional, depending on battery component capacity.

FIG. 1C shows the use of DR cassette 20 in an alternate embodiment of a free-standing exposure mode, without tethered connection and removed from support tray 50 during exposure. Following exposure, DR cassette 20 is restored into position, seated again in tray 50 for wireless transmission of the obtained image data to host processor 26. It should be noted that this embodiment requires considerable on-board power capacity for DR cassette 20, since data acquisition and conversion processing requires a considerable amount of power. For the FIG. 1C embodiment, tray 50 serves only as the wireless communication vehicle for image data obtained just following exposure.

Figure 2A:
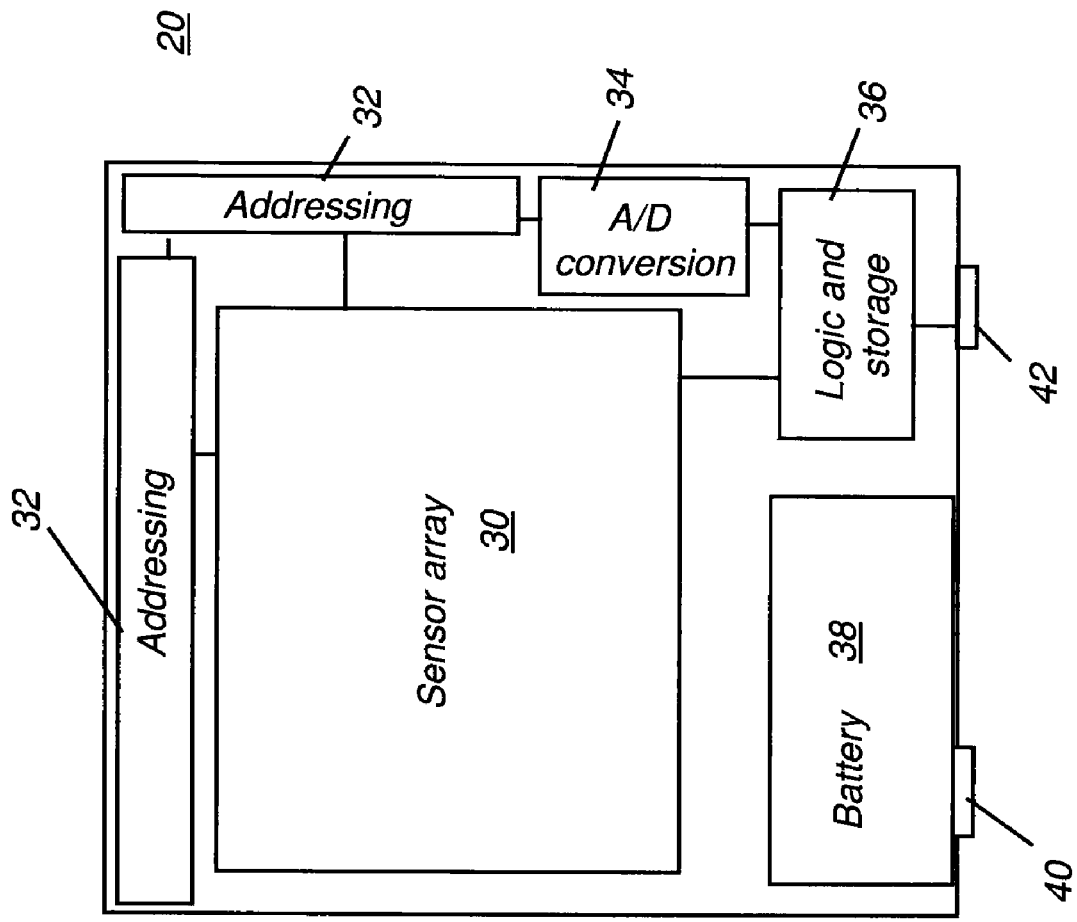
FIG. 2A is a schematic block diagram of the portable DR cassette in one embodiment.

The schematic block diagram of FIG. 2A shows functional components of DR cassette 20 in one embodiment. A sensor array 30 is provided over the sensing area of DR cassette 20, energizable for obtaining energy from the radiation source. Addressing circuitry 32 and Analog-to-Digital (A/D) circuitry 34 provide the components that access and convert signals from sensor array 30 into digital image data and provide the data to logic and storage circuitry 36. In one embodiment, an optional battery or other on-board power supply 38 provides the minimum amount of power needed to energize and support the addressing, data conversion, and storage functions. Interface ports 40 and 42 provide connectors to power supply and data storage components in DR cassette 20. In the embodiment shown, interface port 42 is a data connector; interface port 40 is an input power connector.

It can be appreciated that the arrangement shown in FIG. 2A is one of a number of possible embodiments for DR cassette 20 and that a number of variations are possible from this exemplary embodiment. For example, the supporting circuitry for addressing, data acquisition, processing, and storage can be implemented in a number of ways. In one embodiment, power supply 38 has sufficient capacity for supporting the image data acquisition functions for one or more complete images, allowing image acquisition in stand-alone mode, as was described earlier with reference to FIG. 1C. In other embodiments, power supply 38 does not have this capacity to support data acquisition and conversion functions, but has only enough power to preserve a small amount of stored state and operational status information during periods in which DR cassette 20 is being transferred from one source of operating power to another, such as is needed when using the configuration described for FIG. 1A.

The schematic block diagram of FIG. 2B shows functional components of detector 80, with DR cassette 20 removably seated in support tray 50 in one embodiment. A battery 48 provides source power for energizing DR cassette 20 and may also provide recharge power for power supply 38 on DR cassette 20. A wireless circuit 52 is energizable to transmit the digital image obtained from first data connector of the cassette to external host processor 24 (FIGS. 1B and 1C) and to obtain instructions transmitted wirelessly from host processor 24. Interface ports 44 and 46 provide output power and data connection, respectively, between tray 50 and DR cassette 20 and can be releasably engaged with their counterpart input power and data connectors on DR cassette 20. DR cassette 20 can be removably seated using mechanical latches or can be passively mounted, held in position by restraining features such as brackets and guides built into the body of tray 50 itself or supported in position when connection is made to one or more of its interface port connectors. Advantageously, because tray 50 need not conform to the form factor of earlier film and CR cassettes, battery 48 can be larger and heavier and have higher capacity than the on-board power supply 38 of DR cassette 20.

In one embodiment, DR cassette 20 automatically senses its operating mode for wireless or tethered transmission by sensing a signal provided from support tray 50, such as a signal over interface port 46 or a signal from interface port 44. In an alternate embodiment, DR cassette 20 does not determine its operating mode.

The perspective diagram of FIG. 3A shows how DR cassette 20 is seated to fit into tray 50 in one embodiment of detector 80. Here, tray 50 provides a durable carrying case for DR cassette 20, providing some measure of protection against damage during transport. FIG. 3B shows DR cassette 20 mounted onto tray 50. An optional handle 54 is provided along one of the edges of tray 50 in this embodiment. FIGS. 3C and 3D show a position for handle 54 along the long edge of tray 50 in an alternate embodiment.

The perspective diagram of FIG. 3C shows another embodiment of tray 50 with components provided at two sides of tray 50. FIG. 3D shows the detector 80 assembly with DR cassette 20 seated within tray 50. It can be appreciated that other arrangements are possible, such as having tray 50 with its components mounted along the long edge of DR cassette 20. The arrangement of tray 50 components can be optimized for different types of imaging, such as to allow a corner of DR cassette 20 to be more easily fitted directly against the patient or other subject, for example.

Figure 3E:
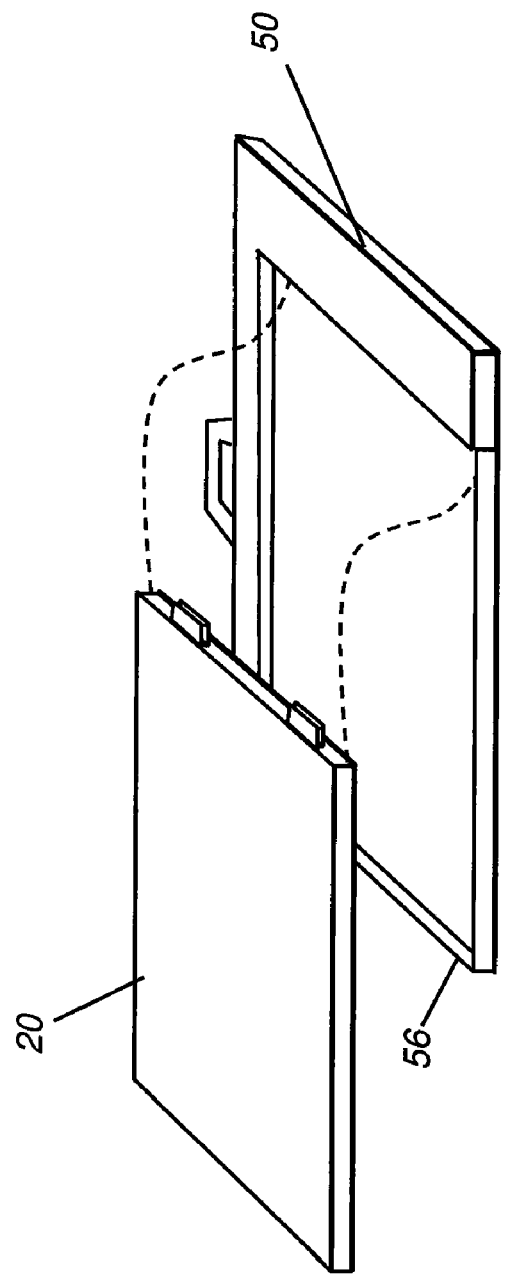
FIG. 3E is a perspective diagram showing how the DR cassette fits into the tray in an alternate embodiment that has thin edge walls.
Figure 3F:
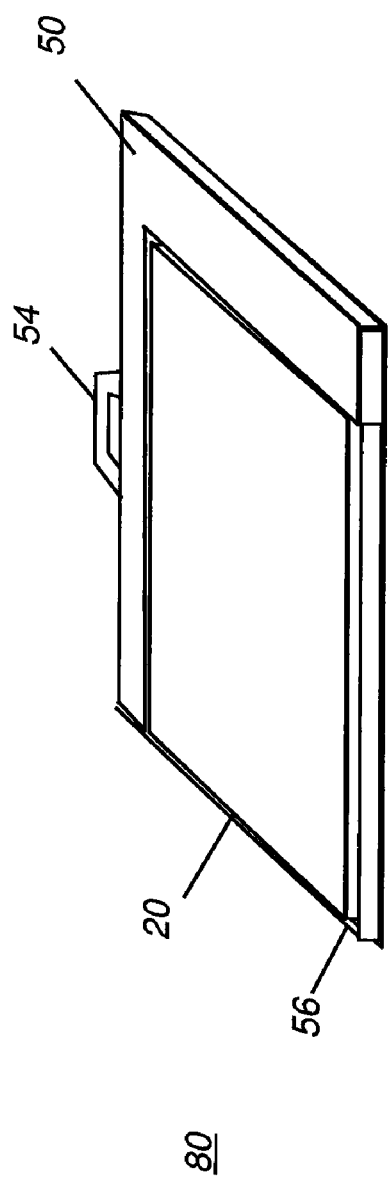
FIG. 3F is a perspective view showing the assembled DR cassette and tray for the embodiment of FIG. 3E.

The perspective diagram of FIG. 3E shows an alternate embodiment of tray 50 with components provided along two edges and with an optional thin wall 56 along one or more other edges of tray 50. FIG. 3F shows detector 80 formed by seating DR cassette 20 into tray 50. Wall 56 helps to retain cassette 20 in the tray and to provide additional protection against damage in transporting and handling cassette 20.

Figure 4:
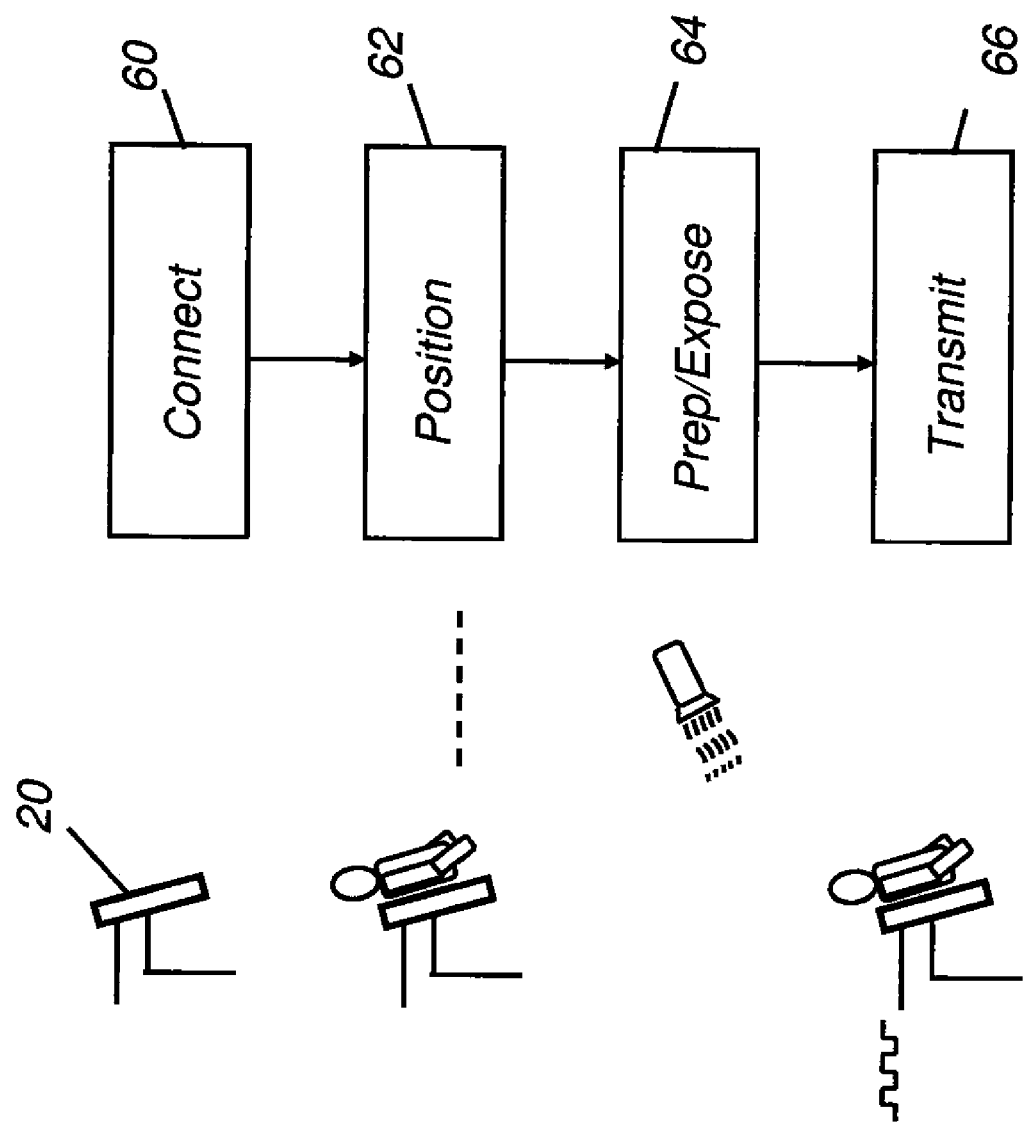
FIG. 4 is a block diagram that shows a sequence for using the DR cassette and tray in the embodiment shown in FIG. 1A.

The block diagram of FIG. 4 shows a sequence for using DR cassette 20 removed from tray 50 in the tethered cassette embodiment shown in FIG. 1A. In a connection step 60, DR cassette 20 is removed from tray 50 and connected to the tethered arrangement of bucky 18. In a positioning step 62, DR cassette 20 is placed near (behind) the subject, patient 14. A preparation and exposure step 64 follows, in which DR cassette 20 is prepared for receiving an image, patient 14 is exposed, and image signals are obtained at the energized sensor array. When imaging at bucky 18 is completed, a transmit step 66 then sends the obtained image data to the host processor over the connected cable. The operator then places DR cassette 20 back into tray 50.

Figure 5:
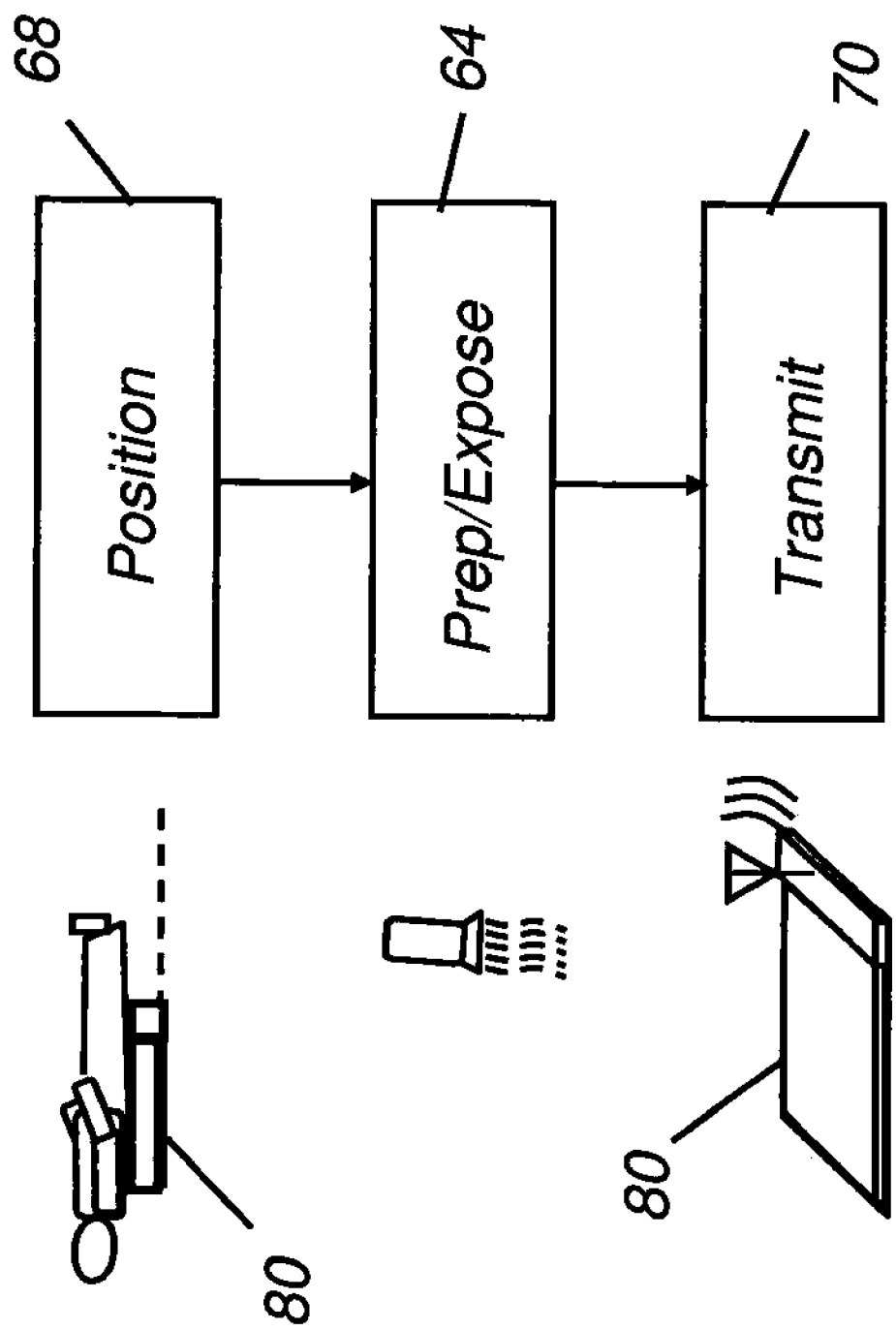
FIG. 5 is a block diagram that shows a sequence for using the DR cassette and tray in the embodiment shown in FIG. 1B.

The block diagram of FIG. 5 shows a sequence for using the combined DR cassette 20 and tray 50 as detector 80 in the embodiment shown in FIG. 1B. In a positioning step 68, detector 80 is placed into position for imaging patient 14. Preparation and exposure step 64 follows, in which, after an initialization of DR cassette 20, patient 14 is exposed and image signals obtained at the sensor array. Image data is then transmitted to host processor 24 from tray 50 in a transmit step 70. Instructions can be provided wirelessly to prompt DR cassette 20 to initiate preparation and exposure processing and to initiate transmission of obtained image data. These instructions may originate from host processor 24 (FIG. 1B). Detector 80 may remain in place behind the patient or may be removed for image data transmission.

Figure 6:
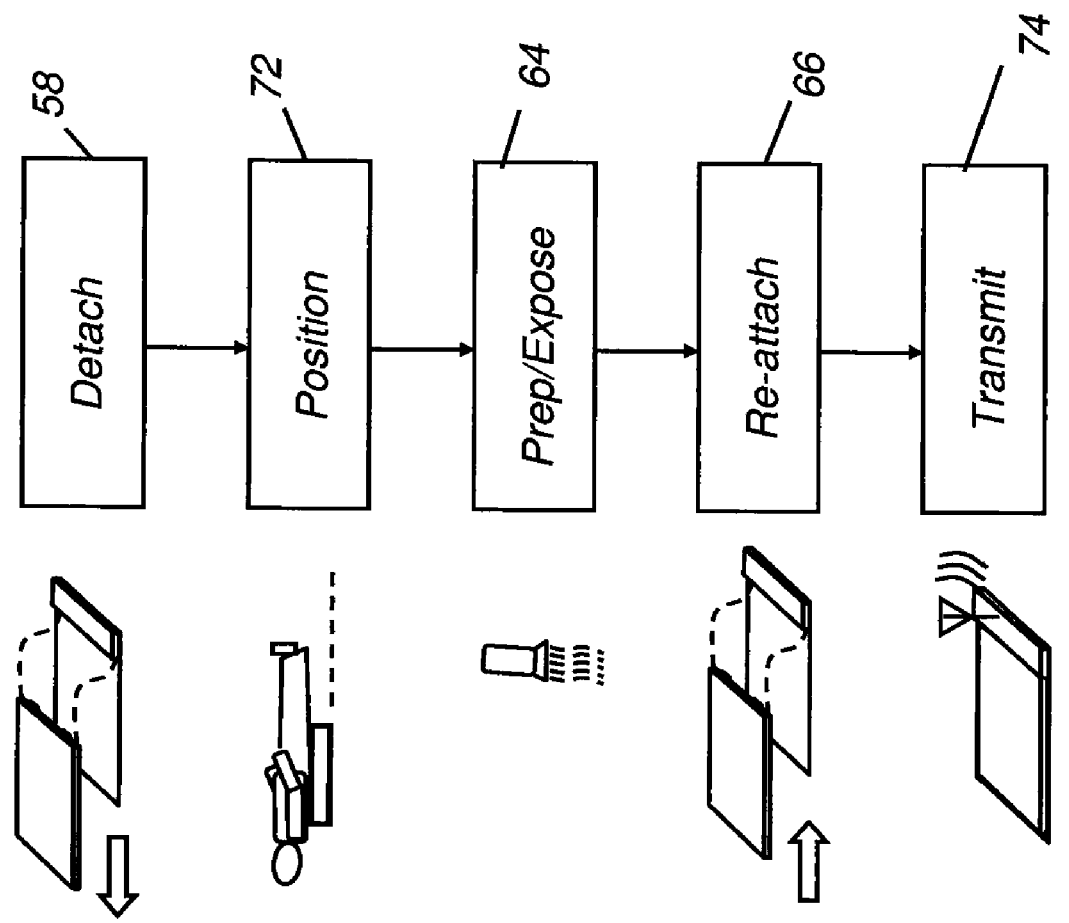
FIG. 6 is a block diagram that shows a sequence for using the DR cassette and tray in the embodiment shown in FIG. 1C.

The block diagram of FIG. 6 shows a sequence for using DR cassette 20 and tray 50 in the embodiment shown in FIG. 1C. In a detach step 58, DR cassette 20 is removed from tray 50. In a positioning step 72, DR cassette 20 is placed into position for imaging patient 14. Preparation and exposure step 64 follows, in which, following preparation of DR cassette 20 to obtain an image, patient 14 is exposed and image signals obtained at the sensor array. When imaging exposure is completed, a re-attach step 66 places DR cassette 20 back into tray 50. Image data is then transmitted to host processor 24 from tray 50 in a transmit step 74.

Tray 50 thus provides a mechanism that allows DR cassette 20 to be used in a number of different possible configurations, either in tethered mode (FIG. 1A) or in an untethered mode, installed in tray 50 to form detector 80 (FIG. 1B) or separate from tray 50 during exposure and re-seated in tray 50 for data transmission (FIG. 1C). This allows flexible use of DR cassette 20, allowing its use as a retrofit with existing DR imaging systems from various manufacturers. With proper engagement of connectors to its interface ports, tray 50 can be used with any of a number of DR cassettes 20 of different dimensions, including cassettes that conform to conventional form factors used for film and CR cassette imaging. Any of a number of mechanisms can be used for providing an instruction to transmit the obtained digital image from tray 50. The data can be sent automatically upon acquisition or as prompted by an instruction entered from remote host processor 24 or entered by a switch setting or other mechanism at tray 50.

The use of tray 50 helps to alleviate some of the requirements for full portability of DR cassette 20, such as the need to have on-board wireless communication circuitry installed within the cassette housing itself. Tray 50 provides a measure of protection against bending, crushing, and dropping during transport and positioning.

In an alternate embodiment, one or more operator controls are provided either on tray 50 itself or through operator commands sent over the wireless communications channel. For example, a "wake-up" or "standby mode" instruction may be entered to put tray 50 into a suitable state, such as for improved power consumption.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, the wireless communication can use radio frequency (RF) communication or infrared or other wireless communication mechanisms that are used for transmitting data. There are a number of types of wireless protocol in current use and familiar to those skilled in the wireless data communication arts, such as IEEE 802.11b and 802.11g, for example.

Thus, what is provided is an apparatus for digital radiography that can be used to transmit obtained digital image data using either tethered or wireless operation.

Parts List 10, 12. Radiographic imaging apparatus
14. Patient

18. Bucky
20. DR cassette
24. Host processor
26. Display
30. Sensor array
32. Addressing circuitry
34. A/D circuitry
36. Logic and storage circuitry
38. Power supply
40, 42, 44, 46. Interface port
48. Battery
50 Tray
52. Wireless interface
54. Handle
56. Wall
58. Detach step
60. Connection step
62. Positioning step
64. Preparation and exposure step
66. Transmit step
68. Positioning step
70. Transmit step
72. Positioning step
74. Transmit step
80. Detector

The invention claimed is:

1. A digital radiography apparatus comprising:
a cassette adapted to obtain a digital image of a subject in response to incident radiation when receiving source power through an input power connector and adapted to provide the obtained digital image as output from a first data connector; and
a support tray adapted to removably seat the cassette comprising:
(1) a second data connector that releasably engages with the first data connector on the cassette when the cassette is seated in the support tray;
(2) a wireless communication circuit that is energizable to transmit the digital image obtained from first data connector of the cassette to a host processor; and
(3) a battery providing source power to at least the wireless communication circuit on the support tray circuitry and the input power connector of the seated cassette.

2. The apparatus of claim 1 wherein the support tray is rectangular and wherein the second data connector, the battery, and the wireless communication circuit are housed along a first edge of the support tray.

3. The apparatus of claim 2 wherein a side wall is formed along at least a second edge of the support tray.

4. The apparatus of claim 3 wherein a side wall is formed along at least one other edge of the support tray.

5. The apparatus of claim 1 wherein the support tray is rectangular and wherein the battery and wireless communication circuit are housed along more than one edge of the support tray.

6. The apparatus of claim 1 wherein the support tray further comprises an output power connector that is adapted to releasably engage with the input power connector of the cassette when the cassette is seated in the support tray.

7. The apparatus of claim 1 wherein the cassette, when removed from the support tray, is dimensioned to fit within a bucky device of an associated radiographic imaging system.

8. The apparatus of claim 1 wherein the cassette is operable in a tethered transmission mode with a power cable connection to the input power connector and a data cable connection to the first data connector; and operable in a wireless transmission mode when the cassette is seated in the support tray.

9. A method for obtaining a digital radiography image of a subject comprising:
seating a digital radiography cassette into a support tray to engage a data connection and a power connection between the digital radiography cassette and the support tray;
positioning the support tray near the subject and exposing the subject to radiation to obtain a digital image at the digital radiography cassette; and
transmitting the obtained digital image to a host processor using wireless communication provided from the support tray.

10. The method of claim 9 further comprising transmitting an instruction to the digital radiography cassette to prepare for exposure.

11. The method of claim 9 wherein said subject is a first subject and said digital image is a first digital image and said host processor is a first host processor, the method further comprising:
removing the digital radiography cassette from the support tray;
positioning the digital radiography cassette into a bucky device and positioning the bucky device near a second subject;
connecting a data cable and a power cable to the digital radiography cassette;
exposing the second subject to radiation to obtain a second digital image at the digital radiography cassette; and
transmitting the obtained digital image to a second host processor over the data cable.

12. An apparatus for digital radiography comprising a cassette adapted to obtain a digital image of a subject in response to incident radiation, wherein the cassette has an input power connector and an output data connector and wherein the cassette is operable in either of at least two modes:
a wireless transmission mode, in which the cassette is seated in a support tray that provides a battery connection to the input power connector and wherein the support tray further provides an input data connector that engages with the output data connector of the cassette for receiving the obtained digital image, and wherein the support tray further comprises a wireless communication circuit for transmission of the obtained digital image; and
a tethered transmission mode, in which the cassette is removed from the support tray, and has a data cable connection to the output data connector for transmission of the obtained digital image.

13. The apparatus of claim 12 wherein the cassette is further operable in a freestanding exposure mode, in which the cassette is removed from the support tray during exposure and seated in the support tray for transmission of the obtained digital image.

14. The apparatus of claim 12 wherein the cassette senses a signal that indicates it is in wireless transmission mode, wherein the tethered transmission mode is configured to use a power cable connection to the input power connector.

15. An apparatus for use in digital radiography of an object, comprising:
a support tray adapted to be positioned to receive radiation from at least a portion of the object;
a cassette including an array of sensors for digitally capturing an image in response to the radiation, the cassette being releasably mounted on the tray;

electronics supported by the tray for releasable connection to the cassette to receive digital output signals from the array of sensors; and at least one releasable connector supported by the tray for releasably connecting the array of sensors to the electronics.

16. The apparatus according the claim 15, wherein the tray is rectangular and the electronics and releasable connector are located along at least one edge of the tray.

17. The apparatus according to claim 16, wherein the tray comprises thin edge walls along its other edges than the at least one edge, whereby the other edges may be positioned close to the object during image capture.

18. The apparatus according to claim 15, wherein the tray is rectangular and comprises a bottom wall with thin surrounding edges; and the electronics and releasable connector are supported by the bottom wall, wherein the cassette is one of a plurality of different cassette sizes.

19. The apparatus according to claim 15, further comprising at least one further releasable connector supported by the tray for releasably connecting the electronics to an associated radiographic imaging system.

20. The apparatus according to claim 15, wherein the tray is sized to fit into a support bucky of an associated radiographic imaging system, interchangeably with a conventional radiographic film cassette.

* * * * *